United States Patent [19]
Cherpeck

[11] Patent Number: 5,622,532
[45] Date of Patent: Apr. 22, 1997

[54] POLYLACTONE AROMATIC ESTERS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 667,060

[22] Filed: Jun. 20, 1996

Related U.S. Application Data

[60] Provisional application No. 60/000,934, Jul. 6, 1995.

[51] Int. Cl.$^6$ .................. C10L 1/18; C10L 1/22
[52] U.S. Cl. .................. 44/389; 44/391; 560/20; 560/22; 560/23; 560/43; 560/61
[58] Field of Search .................. 44/389, 391; 560/20, 560/22, 23, 43, 61

[56] References Cited

U.S. PATENT DOCUMENTS

| | | | |
|---|---|---|---|
| 4,191,537 | 3/1980 | Lewis et al. | 44/71 |
| 4,820,432 | 4/1989 | Lundberg et al. | 252/51.5 A |
| 5,028,667 | 7/1991 | McLain et al. | 525/415 |
| 5,296,003 | 3/1994 | Cherpeck | 44/398 |
| 5,306,314 | 4/1994 | Cherpeck | 44/387 |
| 5,366,517 | 11/1994 | Cherpeck | 44/387 |
| 5,366,519 | 11/1994 | Cherpeck | 44/389 |
| 5,462,567 | 10/1995 | Cherpeck | 44/398 |
| 5,482,522 | 1/1996 | Cherpeck | 44/391 |

OTHER PUBLICATIONS

RN 120091-23-8 HCA 1996 ACS.
RN 120091-22-7 HCA 1996 ACS.
RN 120813-66-3 HCA 1996 ACS.
RN 122957-89-5 HCA 1996 ACS.
RN 122957-88-4 HCA 1996 ACS.
RN 122957-89-5 HCA 1996 ACS.
RN 122957-88-4 HCA 1996 ACS.
RN 71401-70-2 HCA 1996 ACS.
RN 120091-23-8 HCA 1996 ACS.
RN 120813-65-2 HCA 1996 ACS.
P. Dubois et al., "Macromolecular Engineering of Polylactones and Polylactides. 8. Ring–Opening Polymerization of $\epsilon$ –Caprolactone Initiated by Primary Amines and Trialkylaluminum", *Macromolecules*, 1992, Month unknown vol. 25, pp. 2614–2618.
D. Tian et al., "Macromolecular Engineering of Polylactones and Polylactides. 18. Synthesis of Star–Branched Aliphatic Polyesters Bearing Various Functional End Groups", *Macromolecules*, 1994, month unknown vol. 27, pp. 4134–4144.

*Primary Examiner*—Margaret Medley
*Attorney, Agent, or Firm*—Claude J. Caroli

[57] ABSTRACT

Polylactone aromatic esters having the formula:

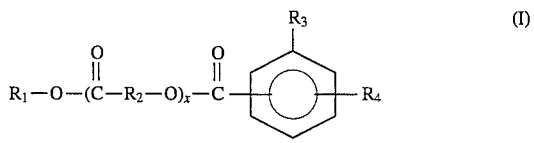

wherein $R_1$ is a hydrocarbyl group having a sufficient number of carbon atoms to render the compound soluble in hydrocarbons boiling in the gasoline or diesel fuel range;

$R_2$ is an alkylene group of about 2 to 5 carbon atoms;

$R_3$ and $R_4$ are each independently hydrogen, hydroxy, nitro, amino, N-alkylamino having 1 to 6 carbon atoms in the alkyl group, or N,N-dialkylamino having 1 to 6 carbon atoms in each alkyl group, provided that $R_3$ and $R_4$ may not both be hydrogen;

and x is an integer from 1 to 25.

The polylactone aromatic esters of formula I are useful as fuel additives for the prevention and control of engine deposits.

29 Claims, No Drawings

POLYLACTONE AROMATIC ESTERS AND FUEL COMPOSITIONS CONTAINING THE SAME

CROSS-REFERENCE TO RELATED APPLICATIONS

This application claims priority from Provisional U.S. application Ser. No. 60/000,934, filed Jul. 6, 1995.

BACKGROUND OF THE INVENTION

1. Field of the Invention

This invention relates to novel end-functionalized polylactones. More particularly, this invention relates to novel polylactone aromatic esters and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, polyether amine fuel additives are well known in the art for the prevention and control of engine deposits. These polyether additives have a poly(oxyalkylene) "backbone", i.e., the polyether portion of the molecule consists of repeating oxyalkylene units. U.S. Pat. No. 4,191,537, issued Mar. 4, 1980 to R. A. Lewis et al., for example, discloses a fuel composition comprising a major portion of hydrocarbons boiling in the gasoline range and from 30 to 2,000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units having from 2 to 5 carbon atoms in each oxyalkylene unit. These fuel compositions are taught to maintain the cleanliness of intake systems without contributing to combustion chamber deposits.

Poly(vinyl ether) amine fuel additives are also known in the art. For example, U.S. Pat. No. 5,306,314 discloses poly(vinyl ether) aminocarbamate fuel additives having a vinly ether polymer backbone consisting of repeating vinyl ether units. These compounds are taught to be useful in fuel compositions to prevent and control engine deposits.

Polylactone polymer compositions have also been reported in the art. For example, U.S. Pat. No. 5,028,667 to McLain et al., discloses a process for the ring-opening polymerization of lactones using as catalysts compounds of yttrium and the rare earth metals. This patent further teaches that the resulting polylactone polymers are useful as biodegradable polymers for medical uses and as flexible films for packaging.

P. Dubois et al., in Macromolecules, 1992, Volume 25, Pages 2614–2618, describe the ring-opening polymerization of caprolactone initiated by primary amines and trialkylaluminum. The resulting polycaprolactone is taught to be useful in the biomedical field due to its high permeability, lack of toxicity for living organisms, biodegradability and capacity to be blended with various commercial polymers over a wide composition range. D. Tian et al., in Macromolecules, 1994, Volume 27, Pages 4134–4144, describe star-branched polycaprolactone polymers having primary amine end groups. These polymers are prepared by the ring-opening polymerization of caprolactone with aluminum alkoxides and a trimesic acid trichloride termination agent.

U.S. Pat. No. 4,820,432 to Lundberg et al. discloses poly ($C_5$ to $C_9$ lactone) modified Mannich base adducts which are prepared by reacting a $C_5$ to $C_9$ lactone, an amine, an aldehyde, an N-hydroxyarylamine, and a hydrocarbyl substituted $C_4$ to $C_{10}$ monounsaturated dicarboxylic acid producing material, such as a polyisobutenyl succinic anhydride. These modified Mannich base adducts may be prepared, for example, by first reacting an N-hydroxyarylamine with a hydrocarbyl substituted dicarboxylic acid producing material to form an N-hydroxyaryl hydrocarbyl substituted imide, which is subsequently reacted with an aldehyde and an amine to form an intermediate Mannich base adduct having an amino functional group capable of initiating lactone ring opening polymerization, and then reacting the intermediate Mannich base adduct with a $C_5$ to $C_9$ lactone. This patent further teaches that the resulting poly ($C_5$ to $C_9$ lactone) modified Mannich base adduct is useful as an oil soluble dispersant additive for fuel and lubricating oil compositions.

It has now been discovered that certain polylactone aromatic esters provide excellent control of engine deposits, especially intake valve deposits, when employed as fuel additives in fuel compositions.

SUMMARY OF THE INVENTION

The present invention provides novel fuel-soluble hydrocarbyl-substituted polylactone aromatic ester fuel additives which are useful for the prevention and control of engine deposits, particularly intake valve deposits.

The fuel-soluble polylactone aromatic esters of the present invention have the formula:

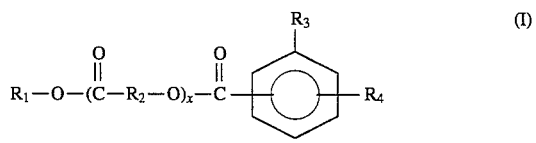

wherein $R_1$ is a hydrocarbyl group having a sufficient number of carbon atoms to render the compound soluble in hydrocarbons boiling in the gasoline or diesel fuel range;

$R_2$ is an alkylene group of about 2 to 5 carbon atoms;

$R_3$ and $R_4$ are each independently hydrogen, hydroxy, nitro, amino, N-alkylamino having 1 to 6 carbon atoms in the alkyl group, or N,N-dialkylamino having 1 to 6 carbon atoms in each alkyl group, provided that $R_3$ and $R_4$ may not both be hydrogen;

and x is an integer from 1 to 25.

The present invention further provides a fuel composition comprising a major amount of hydrocarbons boiling in the gasoline or diesel range and an effective deposit-controlling amount of a polylactone aromatic ester of the present invention.

The present invention additionally provides a fuel concentrate comprising an inert stable oleophilic organic solvent boiling in the range of from about 150° F. to 400° F. (about 65° C. to 205° C.) and from about 10 to 70 weight percent of a polylactone aromatic ester of the present invention.

Among other factors, the present invention is based on the surprising discovery that certain hydrocarbyl-substituted polylactone aromatic esters provide excellent control of engine deposits, especially on intake valves, when employed as fuel additives in fuel compositions.

DETAILED DESCRIPTION OF THE INVENTION

The fuel additives provided by the present invention have the general formula:

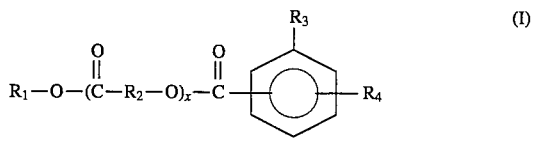

wherein $R_1$, $R_2$, $R_3$, $R_4$ and x are as defined hereinabove.

Preferably, $R_1$ is a hydrocarbyl group having from 1 to about 100 carbon atoms. More preferably, $R_1$ is a hydrocarbyl group having about 3 to about 100 carbon atoms. In a particularly preferred embodiment of the present invention, $R_1$ is an alkyl group having 1 to about 100 carbon atoms or an aralkyl group having 7 to about 100 carbon atoms. More preferably, $R_1$ is alkyl having 1 to about 100 carbon atoms. Still more preferably, $R_1$ is an alkyl group containing about 3 to about 100 carbon atoms.

$R_2$ is preferably an alkylene group having 4 to 5 carbon atoms. More preferably, $R_2$ is an alkylene group having 5 carbon atoms.

Preferably, $R_3$ and $R_4$ are each independently hydrogen, hydroxy, nitro or amino, provided that $R_3$ and $R_4$ may not both be hydrogen. More preferably, $R_3$ is hydroxy, nitro or amino and $R_4$ is hydrogen or hydroxy. Even more preferably, $R_3$ is hydroxy and $R_4$ is hydrogen, or $R_3$ is amino and $R_4$ is hydrogen or hydroxy. Most preferably, $R_3$ is amino and $R_4$ is hydrogen.

When $R_3$ or $R_4$ is N-alkylamino group, the alkyl group of the N-alkylamino moiety preferably contains 1 to 4 carbon atoms. More preferably, the alkyl group is methyl or ethyl. For example, particularly preferred N-alkylamino groups are N-methylamino and N-ethylamino groups. Most preferably, the alkyl group is methyl.

Similarly, when $R_3$ or $R_4$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino, and N,N-diethylamino groups. Most preferably, each alkyl group is methyl.

Preferably, x is an integer from 1 to 10. More preferably, x is an integer from 1 to 5.

A preferred group of polylactone aromatic esters are those of formula I wherein $R_1$ is alkyl or aralkyl having 1 to about 100 carbon atoms; $R_2$ is alkylene having 4 to 5 carbon atoms; $R_3$ is hydroxy, nitro or amino; $R_4$ is hydrogen or hydroxy; and x is an integer from 1 to 10.

It is especially preferred that the hydroxy, nitro, amino, N-alkylamino or N,N-dialkylamino substituent or substituents (i.e., $R_3$ and $R_4$) on the aromatic moiety of the polylactone aromatic esters of this invention be situated in a meta or para position relative to the ester moiety on the aromatic ring. When both $R_3$ and $R_4$ are substituents other than hydrogen, it is also preferred that these substituents be ortho to each other on the aromatic ring, as well as meta or para to the ester moiety. When $R_4$ is hydrogen, it is particularly preferred that the $R_3$ substituent be situated in a para position relative to the ester moiety.

The polylactone aromatic esters of the present invention will generally have a sufficient molecular weight so as to be non-volatile at normal engine intake valve operating temperatures. Typically, the molecular weight of the polylactone aromatic esters of this invention will range from about 250 to about 5,000, preferably from 250 to 3,000.

Fuel-soluble salts of the polylactone aromatic esters of the present invention are also contemplated to be useful for preventing or controlling deposits. For compounds containing a hydroxy group, such salts include alkali metal, alkaline earth metal, ammonium, substituted ammonium, and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Fuel-soluble salts of the polylactone aromatic esters of the present invention can also be readily prepared for those compounds containing an amino, N-alkylamino, or N,N-dialkylamino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein the following terms have the following meanings unless expressly stated to the contrary.

The term "hydrocarbyl" refers to an organic radical primarily composed of carbon and hydrogen which may be aliphatic, alicyclic, or aromatic-substituted aliphatic (e.g. aralkyl). Such hydrocarbyl groups are generally free of aliphatic unsaturation, i.e. olefinic or acetylenic unsaturation, but may contain minor amounts of heteroatoms, such as oxygen or nitrogen, or halogens, such as chlorine.

The term "alkyl" refers to both straight- and branched-chain alkyl groups.

The term "alkylene" refers to straight- and branched-chain alkylene groups having at least 2 carbon atoms. Typical alkylene groups include, for example, ethylene (—$CH_2CH_2$—), propylene (—$CH_2CH_2CH_2$—), isopropylene (—$CH(CH_3)CH_2$—), n-butylene (—$CH_2CH_2CH_2CH_2$—), sec-butylene (—$CH(CH_2CH_3)CH_2$—), n-pentylene (—$CH_2CH_2CH_2CH_2CH_2$—), and the like.

The term "amino" refers to the group: —$NH_2$.

The term "N-alkylamino" refers to the group: —$NHR_a$ wherein $R_a$ is an alkyl group. The term "N,N-dialkylamino" refers to the group: —$NR_bR_c$, wherein $R_b$ and $R_c$ are alkyl groups.

The term "polylactone" refers to a ring-opened lactone polymer having the general formula:

wherein $R_2$ is an alkylene group of 2 to 5 carbon atoms and x is an integer from about 1 to about 25. The term "lactone unit" refers to one monomeric unit of a polylactone polymer. Such polylactone polymers are obtained by the ring-opening polymerization of a lactone. When referring herein to the number of lactone units in a polylactone compound, it is to be understood that this number refers to the average number of lactone units in such compounds unless expressly stated to the contrary.

Also, for purposes of the present invention, the term "polylactone" is meant to include those ring-opened compounds having only about 1 lactone unit, that is, those compounds wherein x is about 1.

General Synthetic Procedures

The polylactone aromatic esters of this invention may be prepared by the following general methods and procedures. It should be appreciated that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxy group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the polylactone aromatic esters of this invention having an amino group on the aromatic moiety will generally be prepared from the corresponding nitro derivative. Accordingly, in many of the following procedures, a nitro group will serve as a protecting group for the amino moiety.

The polylactone aromatic esters of the present invention having the formula:

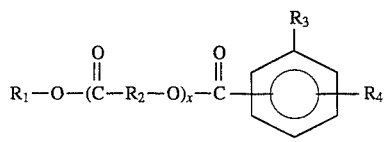     (I)

wherein $R_1$, $R_2$, $R_3$, $R_4$ and x are as defined above, may be prepared by conventional esterification reaction conditions by reacting a polylactone having the formula:

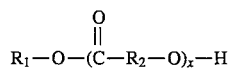     (V)

wherein $R_1$, $R_2$ and x are as defined above, with an aromatic acyl halide having the formula:

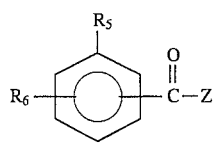     (VII)

wherein $R_5$ and $R_6$ are each independently hydrogen, nitro, N,N-dialkylamino, or a suitably protected hydroxy, amino or N-alkylamino group, provided that $R_5$ and $R_6$ may not both be hydrogen, and Z is a halide, such as chloride or bromide.

Thus, the polylactone aromatic esters of the present invention contain (a) a polylactone component and (b) an aromatic acyl component.

A. The Polylactone Component

The polylactone component of the polylactone aromatic esters of the present invention is a hydrocarbyl-substituted lactone polymer containing about 1 to about 25 lactone units. Generally, the polylactone component will have a hydrocarbyl-substituted lactone unit at one end of the lactone polymer and will be terminated with a hydroxyl group at the other end of the lactone polymer.

The polylactone component of the polylactone aromatic esters of this invention is preferably prepared by polymerizing certain lactone monomers under "living polymerization" conditions. The term "living polymerization" is well known in the art and refers to polymerization reactions which occur in the substantial absence of chain transfer and termination reactions. Under such conditions, the reactive end of the growing polymer is essentially stable indefinitely. Accordingly, each lactone monomer can be added sequentially to the growing polylactone chain in a controlled step-by-step manner. Thus, living polymerization allows polylactones to be prepared having a substantially predictable sequence of lactone units.

In general, the polylactone polymer may be prepared by first reacting an alcohol of the formula:

$$R_1-OH \quad \quad (III)$$

wherein $R_1$ is as defined above, with a suitable lactone polymerization catalyst, such as trialkylaluminum, to form a polymerization initiator which is subsequently reacted with a lactone of the formula:

     (IV)

wherein $R_2$ is as defined above, to provide the desired polylactone having the formula:

     (V)

wherein $R_1$, $R_2$ and x are as defined above.

For example, when employing trimethylaluminum as the polymerization catalyst, the reaction sequence may be described as follows:

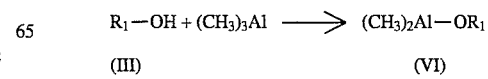

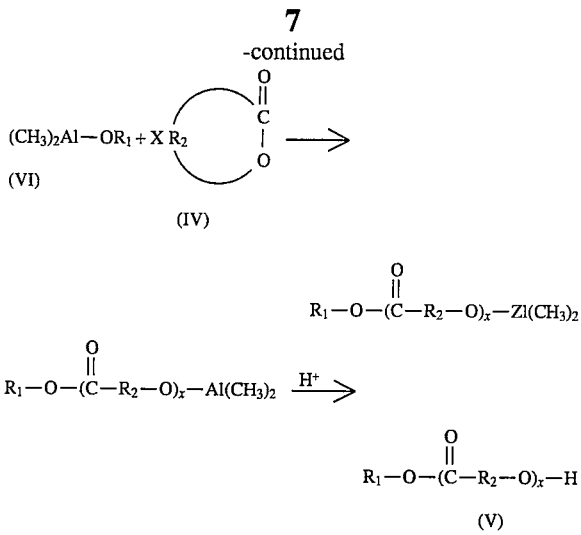

The monohydroxy alcohol compound of formula III, $R_1OH$, used in the above reactions is preferably a straight- or branched-chain alkyl alcohol having 1 to about 100 carbon atoms, more preferably 3 to about 100 carbon atoms; or a straight or branched-chain aralkyl alcohol containing about 7 to about 100 carbon atoms.

Preferred straight-chain alcohols have about 3 to about 30 carbon atoms and include, for example, n-propanol, n-butanol, n-pentanol, n-hexanol, n-heptanol, octanol, nonanol, decanol, hexadecanol (cetyl alcohol), octadecanol (stearyl alcohol) and the like.

Preferred branched-chain alcohols include $C_3$ to $C_{30}$ alcohols such as iso-propanol, sec-butanol, iso-butanol, 3,5,5,-trimethyl hexanol, and the like.

Preferred branched-chain alcohols also include those derived from polymers of $C_2$ to $C_6$ olefins, such as alcohols derived from polypropylene and polybutene. Particularly preferred are polypropylene alcohols having 9 to about 60 carbon atoms and polybutene alcohols having 8 to about 100 carbon atoms. Alcohols derived from the alpha olefin oligomers of $C_8$ to $C_{16}$ alpha olefins, such as the dimer, trimer and tetramer of decene as described in U.S. Pat. No. 4,045,508, issued Aug. 30, 1977 to B. L. Cupples et al., are also useful in this invention.

Many of these straight- and branched-chain alcohols are commercially available and the others can be readily prepared from the corresponding olefins by conventional procedures. Suitable procedures for preparing alcohols from olefins are described for example in I. T. Harrison and S. Harrison, *Compendium of Organic Synthetic Methods*, pp. 119–122, Wiley-Interscience, New York (1971) and references cited therein.

As noted above, the alcohol $R_1OH$ is reacted with a lactone polymerization catalyst to form a polymerization initiator. Suitable lactone polymerization catalysts include alkali and alkaline earth metal hydrides, alkoxides and alkyls; alkyl aluminum and alkyl zinc compounds; alkoxides of aluminum, titanium, zirconium and tin; yttrium and rare earth metal alkoxides; and the like.

Preferred polymerization catalysts for use with the alcohol $R_1OH$ are the trialkylaluminum compounds, such as trimethylaluminum and triethylaluminum.

Generally, the reaction of alcohol $R_1OH$ with the polymerization catalyst will be conducted in a substantially anhydrous inert solvent at a temperature of about −50° C. to about 150° C., preferably −10° C. to 50° C. Suitable inert solvents include benzene, toluene, dichloromethane, diethyl ether and the like. Preferably, the reaction will be conducted under a dry inert gas atmosphere, such as nitrogen or argon, at about atmospheric or ambient pressure. Typically, the molar ratio of alcohol to polymerization catalyst will range from about 0.5:1 to 5:1.

In the second stage of the polymerization process, the reaction product of the alcohol $R_1OH$ and the polymerization catalyst, such as the alcohol-catalyst adduct of formula VI, is reacted with a lactone monomer of formula IV. In this reaction the alcohol-catalyst adduct functions as an initiator for the lactone polymerization.

Suitable lactone monomers for use in the present invention include simple lactones containing from 3 to 6 carbon atoms, such as β-propiolactone, α-methyl-β-propiolactone, β-methyl-β-propiolactone, β-butyrolactone, γ-butyrolactone, γ-valerolactone, δ-valerolactone, δ-caprolactone, ε-caprolactone, and the like. Preferred lactone monomers include δ-valerolactone and ε-caprolactone. An especially preferred lactone monomer is ε-caprolactone.

Typically, the living polymerization reaction will be conducted in a substantially anhydrous inert solvent which may be the same or different than the solvent employed in forming the polymerization initiator. The polymerization reaction temperature will generally be in the range of about −50° C. to 150° C., preferably from about −10° C. to 50° C. Generally, the polymerization reaction will be carried out under a dry, inert gas atmosphere, such as nitrogen or argon, at about atmospheric or ambient pressure.

The molar ratio of lactone monomer to the polymerization initiator, such as the adduct of formula VI, will generally range from about 1:1 to 25:1, preferably from about 1:1 to 10:1, and more preferably from about 1:1 to 5:1.

The time employed for the polymerization reaction can vary over a wide range and will depend to some extent on the reaction temperature and on the lactone monomers used in the polymerization process. Generally, the reaction will be conducted for about 0.05 to about 20 hours, preferably 0.05 to 1.0 hour or until essentially all the lactone monomers have reacted to form polymer.

When essentially all of the lactone monomer has reacted to form the polymer, the reactive terminal end of the polymer is quenched by contacting the reaction mixture with about 1 to about 100 equivalents of an aqueous acid solution, such as aqueous hydrochloric acid. This affords a hydroxy-terminated polylactone of formula V.

The living polymerization of lactones is well known in the art and is further described, for example, in P. Dubois et al., Macromolecules, 1992, Vol. 25, Pages 2614–2618; D. Tian et al., Macromolecules, 1994, Vol. 27, Pages 4134–4144; and K. J. Ivin and T. Saegusa, *Ring-Opening Polymerization*, Vol. 1, Chapter 7, Elsevier, London, 1984, and references cited therein.

The hydroxy-terminated polylactone of formula V may then be coupled with a suitable aromatic acyl component using an appropriate aromatic acyl halide as described in further detail below.

B. Preparation of the Acyl Halide

Acyl halides of formula VII may be prepared from the corresponding aromatic carboxylic acids by first protecting the hydroxy or amino groups as necessary to form a carboxylic acid having the formula:

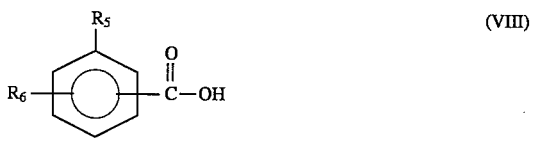

(VIII)

wherein $R_5$ and $R_6$ are as defined above.

The aromatic carboxylic acids which are first protected and then converted to the corresponding acyl halide are either known compounds or can be prepared from known compounds by conventional procedures. Representative aromatic carboxylic acids suitable for use as starting materials include, for example, 2-hydroxybenzoic acid, 3-hydroxybenzoic acid, 4-hydroxybenzoic acid, 3,4-dihydroxybenzoic acid, 2-nitrobenzoic acid, 3-nitrobenzoic acid, 4-nitrobenzoic acid, 3-hydroxy-4-nitrobenzoic acid, 4-hydroxy-3-nitrobenzoic acid, 2-aminobenzoic acid (anthranilic acid), 3-aminobenzoic acid, 4-aminobenzoic acid, 3-amino-4-hydroxybenzoic acid, 4-amino-3-hydroxybenzoic acid, 3-(N-methylamino)benzoic acid, 4-(N-methylamino)benzoic acid, 3-(N-ethylamino)benzoic acid, 4-(N-ethylamino)benzoic acid, 3-(N,N-dimethylamino)benzoic acid, 4-(N,N-dimethylamino)benzoic acid, and the like.

Preferred aromatic carboxylic acids include 3-hydroxybenzoic acid, 4-hydroxybenzoic acid, 3-nitrobenzoic acid, 4-nitrobenzoic acid, 3-hydroxy-4-nitrobenzoic acid, 4-hydroxy-3-nitrobenzoic acid, 3-aminobenzoic acid, 4-aminobenzoic acid, 3-amino-4-hydroxybenzoic acid, and 4-amino-3-hydroxybenzoic acid. Particularly preferred aromatic carboxylic acids include 4-aminobenzoic acid, 4-hydroxybenzoic acid and 4-amino-3-hydroxybenzoic acid.

When the aromatic carboxylic acid contains a hydroxy group, for example, 4-hydroxybenzoic acid, protection of the aromatic hydroxy groups may be accomplished using well-known procedures. The choice of a suitable protecting group for a particular hydroxy aromatic carboxylic acid will be apparent to those skilled in the art. Various protecting groups, and their introduction and removal, are described, for example, in T. W. Greene and P. G. M. Wuts, *Protective Groups in Organic Synthesis*, Second Edition, Wiley, New York, 1991, and references cited therein.

Deprotection of the aromatic hydroxy group(s) can also be accomplished using conventional procedures. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

When synthesizing the polylactone aromatic esters of formula I having an amino group on the aromatic moiety (i.e., where $R_3$ or $R_4$ is an amino group), it is generally desirable to first prepare the corresponding nitro compound (i.e., where $R_3$ or $R_4$ is a nitro group) and then to reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron, and the like, in the presence of an acid, such as dilute hydrochloric acid.

Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate, toluene, and the like. Hydrogenation of aromatic nitro groups is discussed in further detail in, for example, P. N. Rylander, *Catalytic Hydrogenation in Organic Synthesis*, pp. 113–137, Academic Press (1979); and *Organic Synthesis*, Collective Vol. I, Second Edition, pp. 240–241, John Wiley & Sons, Inc. (1941); and references cited therein.

The acyl halide of formula VII may then be prepared by reacting the protected aromatic carboxylic acid with an inorganic halide, such as thionyl chloride, phosphorous trichloride, phosphorous tribromide, or phosphorous pentachloride; or with oxalyl chloride, using conventional procedures.

Typically, this reaction will be conducted using about 1 to 5 molar equivalents of the inorganic acyl halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

C. Preparation of the Polylactone Aromatic Esters

Reaction of the acyl halide of formula VII with a polylactone of formula V provides a polylactone aromatic ester of formula I.

Typically, this reaction is conducted by contacting a polylactone of formula V with about 1.0 to about 3.5 molar equivalents of an acyl halide of formula VII in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine base capable of neutralizing the acid generated during the reaction, such as triethylamine, di(isopropyl)ethylamine, pyridine, or 4-dimethylamino-pyridine.

Fuel Compositions

The polylactone aromatic esters of the present invention are useful as additives in hydrocarbon fuels to prevent and control engine deposits, particularly intake valve deposits. Typically, the desired deposit control will be achieved by operating an internal combustion engine with a fuel composition containing a polylactone aromatic ester of the present invention. The proper concentration of additive necessary to achieve the desired deposit control varies depending upon the type of fuel employed, the type of engine, and the presence of other fuel additives.

In general, the concentration of the polylactone aromatic esters of this invention in hydrocarbon fuel will range from about 50 to about 2,500 parts per million (ppm) by weight, preferably from 75 to 1,000 ppm. When other deposit control additives are present, a lesser amount of the present additive may be used. Furthermore, lower concentrations of, for example, 30 to 70 ppm may be preferred when the present additives are employed as carburetor detergents only.

The polylactone aromatic esters of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 10 to 25 weight percent.

In gasoline fuels, other fuel additives may be employed with the additives of the present invention, including, for example, oxygenates, such as t-butyl methyl ether, anti-knock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the polylactone aromatic esters of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478, and in European Patent Application Nos. 356,726 and 382,159.

These carrier fluids are believed to act as a carrier for the fuel additives of the present invention and to assist in removing and retarding deposits. The carrier fluid may also exhibit synergistic deposit control properties when used in combination with the polylactone aromatic esters of this invention.

The carrier fluids are typically employed in amounts ranging from about 100 to about 5,000 ppm by weight of the hydrocarbon fuel, preferably from 400 to 3,000 ppm of the fuel. Preferably, the ratio of carrier fluid to deposit control additive will range from about 0.5:1 to about 10:1, more preferably from 2:1 to 5:1, most preferably about 4:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof and should not be interpreted as limitations upon the scope of the invention.

Example 1

Preparation of

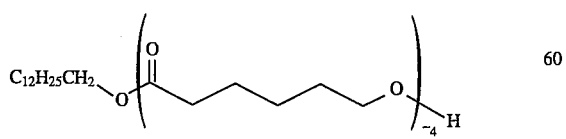

Trimethylaluminum (50.0 mL of a 2.0M solution in toluene) was added to anhydrous dichloromethane (200 mL) via syringe under nitrogen. The solution was cooled to 0° C. and Exxal 13 alcohol (20 grams) was added dropwise. The reaction was stirred at room temperature for 30 minutes and then cooled back to 0° C. ε-Caprolactone (44.3 mL) was added all at once, the cooling bath was removed and the reaction was stirred at room temperature for sixteen hours. The reaction was quenched with 100 mL of 5% aqueous hydrochloric acid and was extracted three times with dichloromethane. The combined organic layers were dried over anhydrous magnesium sulfate, filtered and the solvents removed in vacuo to yield the desired product as a white wax.

Example 2

Preparation of

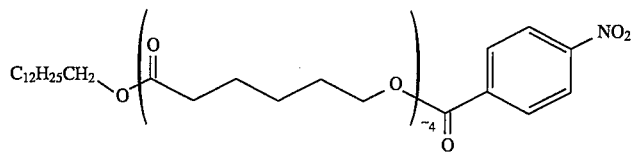

4-Nitrobenzoyl chloride (3.9 grams), the alcohol from Example 1 (16.0 grams), 4-dimethylaminopyridine (2.7 grams) and anhydrous dichloromethane (200 mL) were combined. The resulting mixture was stirred at room temperature under nitrogen for 16 hours. The reaction was diluted with 600 mL of dichloromethane and was washed twice with saturated aqueous sodium bicarbonate solution, twice with 10% aqueous sodium hydroxide solution and once with brine. The organic layer was dried over anhydrous magnesium sulfate, filtered and the solvents removed in vacuo to yield the desired product as a yellow wax. $^1$H NMR (CDCl$_3$) δ 8.3 (AB quartet, 4H), 4.45 (t, 2H), 4.0 (t, 8H), 2.3 (t, 8H), 0.7–1.8 (m, 49H).

Example 3

Preparation of

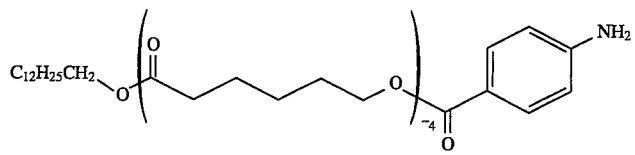

A solution of 10.0 grams of the product from Example 2 in 100 mL of ethyl acetate containing 1.5 grams of 10% palladium on charcoal was hydrogenolyzed at 35–40 psi for 16 hours on a Parr low-pressure hydrogenator. Catalyst filtration and removal of the solvent in vacuo yielded 9.5 grams of the desired product. $^1$H NMR (CDCl$_3$) δ 7.9, 6.75 (AB quartet, 4H), 4.45 (t, 2H), 4.0 (t, 8H), 2.3 (t, 8H), 0.7–1.8 (m, 49H).

Example 4

Preparation of

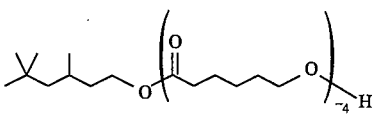

Trimethylaluminum (520 mL of a 2.0M solution in toluene) was added to anhydrous dichloromethane (2 L) via syringe under nitrogen. The solution was cooled to 0° C. and 3,5,5-trimethylhexanol (182 mL) was added dropwise. The reaction was stirred at room temperature for 30 minutes and then cooled back to 0° C. ε-Caprolactone (461 mL) was added all at once, the cooling bath was removed and the reaction was stirred at room temperature for sixteen hours. The reaction was quenched with one liter of 5% aqueous hydrochloric acid and was extracted three times with dichloromethane. The combined organic layers were dried over anhydrous magnesium sulfate, filtered and the solvents removed in vacuo to yield 596 grams of the desired product as a light yellow wax.

Example 5

Preparation of

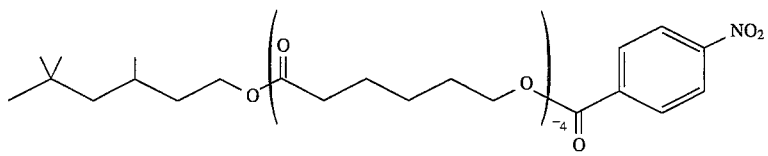

4-Nitrobenzoyl chloride (6.7 grams), the alcohol from Example 4 (15.0 grams), 4-dimethylaminopyridine (4.8 grams) and anhydrous dichloromethane (150 mL) were combined. The resulting mixture was stirred at room temperature under nitrogen for 16 hours. The reaction was diluted with 400 mL of dichloromethane and was washed twice with saturated aqueous sodium bicarbonate solution, twice with 10% aqueous sodium hydroxide solution and once with brine. The organic layer was dried over anhydrous magnesium sulfate, filtered and the solvents removed in vacuo to yield 16.7 grams of the desired product as a yellow oil. $^1$H NMR (CDCl$_3$) δ 8.25 (AB quartet, 4H), 4.4 (t, 2H), 4.0 (t, 8H), 2.3 (t, 8H), 0.7–1.8 (m, 41H).

Example 6

Preparation of

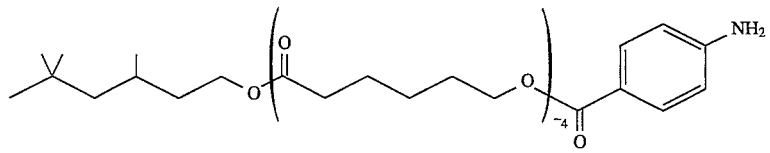

A solution of 12.0 grams of the product from Example 5 in 200 mL of ethyl acetate containing 2.0 grams of 10% palladium on charcoal was hydrogenolyzed at 35–40 psi for 16 hours on a Parr low-pressure hydrogenator. Catalyst filtration and removal of the solvent in vacuo yielded 10.9 grams of the desired product as a colorless oil. $^1$H NMR (CDCl$_3$) δ 7.9, 6.65 (AB quartet, 4H), 4.3 (t, 2H), 4.0 (t, 8H), 2.3 (t, 8H), 0.7–1.8 (m, 41H).

Example 7

Preparation of

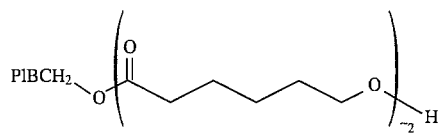

Trimethylaluminum (111 mL of a 2.0M solution in toluene) was added to anhydrous dichloromethane (700 mL) via syringe under nitrogen. The solution was cooled to 0° C. and polyisobutanol (210.4 grams, molecular weight average 984, prepared via hydroformylation of Amoco H-100 polyisobutene) dissolved in 800 mL of anhydrous dichloromethane was added dropwise. The reaction was stirred at room temperature for 30 minutes and then cooled back to 0° C. ε-Caprolactone (49.1 mL) was added all at once, the cooling bath was removed and the reaction was stirred at room temperature for sixteen hours. The reaction was quenched with 1 L of 5% aqueous hydrochloric acid and was extracted three times with dichloromethane. The combined organic layers were dried over anhydrous magnesium sulfate, filtered and the solvents removed in vacuo to yield 250.3 grams of the desired product as a white wax.

Example 8

Preparation of

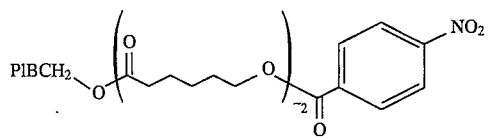

4-Nitrobenzoyl chloride (22.8 grams), the alcohol from Example 7 (130.0 grams), 4-dimethylaminopyridine (16.4 grams) and anhydrous dichloromethane (1.2 L) were combined. The resulting mixture was stirred at room temperature under nitrogen for 16 hours. The reaction was diluted with 2 L of dichloromethane and was washed twice with saturated aqueous sodium bicarbonate solution, twice with 10% aqueous sodium hydroxide solution and once with brine. The organic layer was dried over anhydrous magnesium sulfate, filtered and the solvents removed in vacuo to yield 130.7 grams of the desired product as a yellow oil.

Example 9

Preparation of

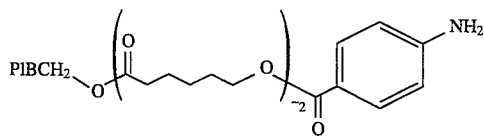

A solution of 130.7 grams of the product from Example 8 in 1.2 L of ethyl acetate containing 2.0 grams of 10% palladium on charcoal was hydrogenolyzed at 35–40 psi for 16 hours on a Parr low-pressure hydrogenator. Catalyst filtration and removal of the solvent in vacuo yielded 116.7 grams of the desired product as a yellow oil. $^1$H NMR (CDCl$_3$) δ 7.9, 6.65 (AB quartet, 4H), 4.3 (t, 2H), 4.0 (t, 4H), 2.3 (t, 4H), 0.6–1.8 (m, 149H).

Example 10

Single-Cylinder Engine Test

The test compounds were blended in gasoline and their deposit reducing capacity determined in an ASTM/CFR single-cylinder engine test. A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I.

TABLE I

Single-Cylinder Engine Test Results

| Sample[1] | Intake Valve Deposit Weight (in milligrams) | | |
|---|---|---|---|
| | Run 1 | Run 2 | Average |
| Base Fuel | 300.1 | 302.3 | 301.2 |
| Example 2 | 156.2 | 160.1 | 158.2 |
| Example 3 | 22.3 | 28.4 | 25.4 |
| Example 5 | 153.5 | 179.8 | 166.7 |
| Example 6 | 18.1 | 16.5 | 17.3 |
| Example 9 | 21.4 | 16.9 | 19.2 |

[1]At 150 parts per million actives (ppma).

The base fuel employed in the above single-cylinder engine tests was a regular octane unleaded gasoline containing no fuel detergent. The test compounds were admixed with the base fuel to give a concentration of 150 ppma (parts per million actives).

The data in Table I illustrates the significant reduction in intake valve deposits provided by a polylactone aromatic ester of the present invention (Examples 2, 3, 5, 6 and 9) compared to the base fuel.

What is claimed is:

1. A fuel composition comprising a major amount of hydrocarbons boiling in the gasoline or diesel fuel range and an effective deposit-controlling amount of a fuel-soluble compound of the formula:

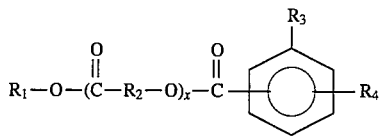

wherein $R_1$ is a hydrocarbyl group having a sufficient number of carbon atoms to render the compound soluble in hydrocarbons boiling in the gasoline or diesel fuel range;

$R_2$ is an alkylene group of about 2 to 5 carbon atoms;

$R_3$ and $R_4$ are each independently hydrogen, hydroxy, nitro, amino, N-alkylamino having 1 to 6 carbon atoms in the alkyl group, or N,N-dialkylamino having 1 to 6 carbon atoms in each alkyl group, provided that $R_3$ and $R_4$ may not both be hydrogen;

and x is an integer from 1 to 25.

2. The fuel composition according to claim 1, wherein $R_1$ is a hydrocarbyl group having from 1 to about 100 carbon atoms.

3. The fuel composition according to claim 1, wherein $R_1$ is an alkyl or aralkyl group.

4. The fuel composition according to claim 3, wherein $R_1$ is an alkyl group.

5. The fuel composition according to claim 1, wherein $R_2$ is an alkylene group of about 4 to 5 carbon atoms.

6. The fuel composition according to claim 5, wherein $R_2$ is an alkylene group of 5 carbon atoms.

7. The fuel composition according to claim 1, wherein x is an integer of from 1 to 10.

8. The fuel composition according to claim 1, wherein $R_3$ and $R_4$ are each independently hydrogen, hydroxy, nitro or amino, provided that $R_3$ and $R_4$ may not both be hydrogen.

9. The fuel composition according to claim 8, wherein $R_3$ is hydroxy, nitro or amino and $R_4$ is hydrogen or hydroxy.

10. The fuel composition according to claim 9, wherein $R_3$ is amino and $R_4$ is hydrogen or hydroxy.

11. The fuel composition according to claim 10, wherein $R_3$ is amino and $R_4$ is hydrogen.

12. The fuel composition according to claim 8, wherein $R_3$ is hydroxy and $R_4$ is hydrogen.

13. The fuel composition according to claim 1, wherein $R_3$ and $R_4$ are in a meta or para position relative to the ester moiety on the aromatic ring.

14. The fuel composition according to claim 1, wherein the composition contains about 50 to about 2500 parts per million by weight of the fuel-soluble compound.

15. The fuel composition according to claim 1, wherein the composition further contains about 100 to about 5000 parts per million by weight of a fuel-soluble, nonvolatile carrier fluid.

16. A fuel concentrate comprising an inert stable oleophilic organic solvent boiling in the range of from about 150° F. to 400° F. and from about 10 to about 70 weight percent of a fuel-soluble compound of the formula:

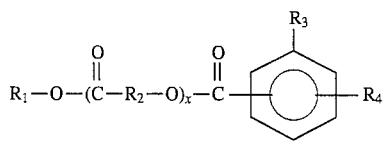

wherein $R_1$ is a hydrocarbyl group having a sufficient number of carbon atoms to render the compound soluble in hydrocarbons boiling in the gasoline or diesel fuel range;

$R_2$ is an alkylene group of about 2 to 5 carbon atoms;

$R_3$ and $R_4$ are each independently hydrogen, hydroxy, nitro, amino, N-alkylamino having 1 to 6 carbon atoms in the alkyl group, or N,N-dialkylamino having 1 to 6 carbon atoms in each alkyl group, provided that $R_3$ and $R_4$ may not both be hydrogen;

and x is an integer from 1 to 25.

17. The fuel concentrate according to claim 16, wherein $R_1$ is a hydrocarbyl group having from 1 to about 100 carbon atoms.

18. The fuel concentrate according to claim 16, wherein $R_1$ is an alkyl or aralkyl group.

19. The fuel concentrate according to claim 18, wherein $R_1$ is an alkyl group.

20. The fuel concentrate according to claim 16, wherein $R_2$ is an alkylene group of about 4 to 5 carbon atoms.

21. The fuel concentrate according to claim 20, wherein $R_2$ is an alkylene group of 5 carbon atoms.

22. The fuel concentrate according to claim 16, wherein x is an integer of from 1 to 10.

23. The fuel concentrate according to claim 16, wherein $R_3$ and $R_4$ are each independently hydrogen, hydroxy, nitro or amino, provided that $R_3$ and $R_4$ may not both be hydrogen.

24. The fuel concentrate according to claim 23, wherein $R_3$ is hydroxy, nitro or amino and $R_4$ is hydrogen or hydroxy.

25. The fuel concentrate according to claim 24, wherein $R_3$ is amino and $R_4$ is hydrogen or hydroxy.

26. The fuel concentrate according to claim 25, wherein $R_3$ is amino and $R_4$ is hydrogen.

27. The fuel concentrate according to claim 26, wherein $R_3$ is hydroxy and $R_4$ is hydrogen.

28. The fuel concentrate according to claim 16, wherein $R_3$ and $R_4$ are in a meta or para position relative to the ester moiety on the aromatic ring.

29. The fuel concentrate according to claim 16, wherein the fuel concentrate further contains about 20 to about 60 weight percent of a fuel-soluble, nonvolatile carrier fluid.

* * * * *